(12) United States Patent
Zak et al.

(10) Patent No.: US 7,987,102 B2
(45) Date of Patent: Jul. 26, 2011

(54) HEALTHCARE PROVIDER PERFORMANCE AND UTILIZATION ANALYTICS

(76) Inventors: Solomon J. Zak, St. Louis Park, MN (US); Rudra Duddala, Westboro, MA (US); Craig Johnson, Cambridge, MN (US); Poladas James, Worcester, MA (US)

(*) Notice: Subject to any disclaimer, the term of this patent is extended or adjusted under 35 U.S.C. 154(b) by 759 days.

(21) Appl. No.: 11/973,754

(22) Filed: Oct. 10, 2007

(65) Prior Publication Data

US 2009/0099865 A1    Apr. 16, 2009

(51) Int. Cl.
*G06Q 50/00* (2006.01)
*G06Q 10/00* (2006.01)

(52) U.S. Cl. ............................................ 705/2; 705/3
(58) Field of Classification Search .................. 705/2–3
See application file for complete search history.

(56) References Cited

U.S. PATENT DOCUMENTS

| | | | | |
|---|---|---|---|---|
| 5,652,842 A | * | 7/1997 | Siegrist et al. | 705/2 |
| 2002/0111826 A1 | * | 8/2002 | Potter et al. | 705/2 |
| 2003/0233323 A1 | * | 12/2003 | Bilski et al. | 705/40 |

OTHER PUBLICATIONS

Schultz, Do employees use report cards to assess health care provider systems?, Health Serv Res. Jul. 2001; 36(3): 509-530.*

* cited by examiner

*Primary Examiner* — Luke Gilligan
*Assistant Examiner* — Tran Nguyen
(74) *Attorney, Agent, or Firm* — Ash Tankha; Lipton, Weinberger & Husick

(57) ABSTRACT

Disclosed herein is a computer implemented method and system that addresses the need for utilization analysis and performance evaluation of providers in a health care organization. The health care data comprising health plan information of consumers, providers, claims, and hospitals is collected, translated, and organized in a structured relational format and stored in standard tables. The organized health care data is analyzed by calculating consumer statistics for a health plan using the health plan information of the consumers. The claims of the consumers are processed to classify the claims based on age, gender, disease, and comorbid conditions of the consumers. A plurality of costs of the health care organization is determined using one or more of the health plan information. The performance of the providers is assessed using the determined plurality of costs. The providers comprising primary care physicians are analyzed based on entire population of the associated consumers.

24 Claims, 2 Drawing Sheets

HEALTHCARE PROVIDER PERFORMANCE AND UTILIZATION ANALYTICS

BACKGROUND

This invention, in general, relates to a health care organization. More particularly, this invention relates to utilization analysis and performance evaluation of providers in the health care organization.

Health care organizations, typically, comprise providers for providing health care services to consumers who enroll for a health plan of the health care organization. The operations of a health care organization depends on one or more factors including the number of consumers that enroll for the health plans, performance of the service providers, quality of the service provided by the service providers, management and utilization of the resources of the health care organization, etc. For an efficient operation of the health care organization, it is important to analyze the performance and quality of the service provider rendering health care services to the consumers. Furthermore, the cost of operation of the health care organization for providing health care services to the consumers in a plurality of health plans needs to be determined. Hence, there is an unmet need for a computer implemented method of effective utilization analysis and performance evaluation of providers in the health care organization.

SUMMARY OF THE INVENTION

The computer implemented method and system disclosed herein addresses the need for utilization analysis and performance evaluation of providers in a health care organization.

The computer implemented method and system disclosed herein is used to collect health care data. The health care data comprises health plan information of consumers, providers, claims, and hospitals. The consumers are one of an individual member, a medicare member, a medicaid member, and an employer. The employer provides health care benefits to a plurality of employees through the health plan. Further, the providers are one of a primary care physician, a procedurally related group specialist, and a medically related group specialist. The step of translating the collected health care data comprises creating file layouts, mapping fields of the health care data, and verifying the integrity and the validity of the health care data. The health care data is organized in a structured relational format in a plurality of standard tables. The plurality of standard tables comprises a consumer data table, a provider data table, a claims data table, a hospital data table, a global table, a parameter table, and a proprietary table.

Further, the computer implemented method and system disclosed herein analyzes the organized health care data for utilization analysis and performance evaluation of the providers. The organized health care data is analyzed by calculating consumer statistics for a health plan using the health plan information of the consumers. The claims of the consumers are processed to classify the claims based on age, gender, disease, and comorbid conditions of the consumers. A plurality of costs of the health care organization are determined using one or more of the health plan information of the consumers, the providers, the claims, and the hospitals. The performance of the providers is assessed using the determined plurality of costs. The providers comprising primary care physicians are analyzed based on the entire population of the consumers associated with the primary care physicians. The computer implemented method and system disclosed herein further comprises the step of generating reports of comparative relative value unit utilization for primary care physicians.

BRIEF DESCRIPTION OF THE DRAWINGS

The foregoing summary, as well as the following detailed description of the embodiments, is better understood when read in conjunction with the appended drawings. For the purpose of illustrating the invention, exemplary constructions of the invention are shown in the drawings. However, the invention is not limited to the specific methods and instrumentalities disclosed herein.

DETAILED DESCRIPTION OF THE INVENTION

Figure 1:
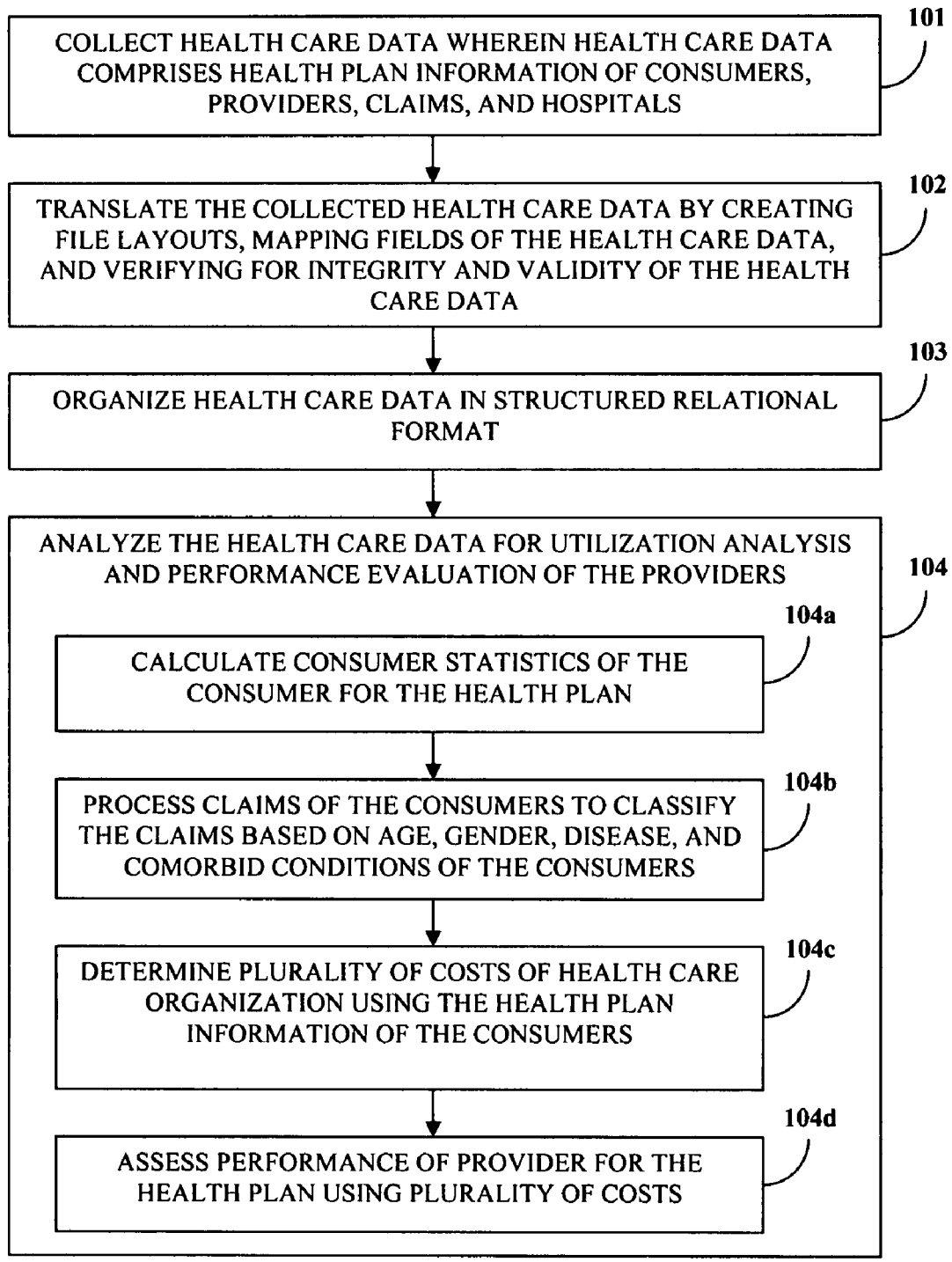
FIG. 1 illustrates a method of utilization analysis and performance evaluation of providers in a health care organization.

FIG. 1 illustrates a method of utilization analysis and performance evaluation of providers in a health care organization. The computer implemented method disclosed herein comprises the step of collecting 101 health care data. The health care data comprises health plan information of consumers, providers, claims, and hospitals. The consumers are one of an individual member, a medicare member, a medicaid member, and an employer. The employer provides health care benefits to a plurality of employees through a health plan. The collected raw health care data is translated 102 and organized 103 into a structured relational format. During the translation of the raw health care data file layouts for the health care data are created and different fields of the health care data are mapped. Further, the integrity and validity of the health care data is verified.

The translated health care data is organized in a plurality of tables in the structured relational format. The plurality of tables is one of translated consumer data tables, provider data tables, claims data tables, hospital data tables, global tables, parameter tables, and proprietary tables. The global tables comprise information about a plurality of standard codes such as current procedure terminology (CPT) code, international classification of diseases (ICD9) diagnosis code, a health care common procedure coding system (HCPCS) code, a revenue code, an ICD9 procedure code, a national drug classification (NDC) code, and a diagnosis related groups (DRG) code. The CPT code includes descriptions of health care services. The ICD code includes the international code for diseases. The HCPCS codes are used for reporting supplies, prosthetic devices, and durable medical equipment. The NDC code is used for identifying drug products. The DRG codes provide a patient classification scheme that is used to relate the type of patients a hospital treats to the costs incurred by the hospital.

The parameter tables comprise date tables, quarters, line of business tables, process tables, and processing order information table. The Line of Business tables comprise medicare table, medicaid table, and commercial table. The proprietary tables comprise disease categories table, disease subcategories table, service categories table, case-mix mapping tables, NDC mapping tables, procedurally related group (PRG) case tables, medically related group (MRG) case tables, PRG exclude tables, MRG exclude tables, PRG include tables, MRG include tables, ICD category table, ICD sub category table, age and gender table of the consumers, CPT group tables, precedent tables for MRG, etc. The health care data is analyzed for identifying the fields in the health care data provided by the health plan or a physician group providing health care services. During the translation of the raw health care data, normalized tables for the health care data are created. The links between the different fields of the normalized tables are created. The data integrity of the health care data is verified. The format of the health care data is converted from extended binary coded decimal interchange code (EBCDIC) to a predefined data format. The normalized data tables with converted health care data are further indexed. The health care data is used for determining enrollment period of the consumers. Further, the health care data is used for identifying financial data, provider specialties, and health care services provided to the consumers.

The computer implemented method disclosed herein analyzes 104 health care data for utilization analysis and performance evaluation of the providers. The providers are one of a primary care physician (PCP), a procedurally related group (PRG) specialist, and a medically related group (MRG) specialist. The computer implemented method disclosed herein calculates 104a consumer statistics for a health plan using the health plan information of the consumers. The consumer statistics is calculated based on age, gender, and disease conditions of the consumers in relation with the primary care physicians, the employer groups, and the primary care physician networks. The step of calculating the consumer statistics includes calculating the period of enrollment of the consumer. Exemplarily, the member months of the consumers are calculated based on the number of months the consumers are enrolled with the PCP in the health plan. The calculation of consumer statistics of the consumers for the health plan is performed periodically. For example, the number of consumers enrolled by the PCPs, employer groups, and the PCP networks maybe calculated on a monthly or a quarterly basis.

Further, the claims of the consumers are processed 104b to classify the claims based on age, gender, disease, and comorbid conditions of the consumers. The classified claims are used to identify disease conditions having maximum claim amount. The process of identifying all the disease conditions related to the claims comprise the step of checking the disease conditions against the CPT and the ICD codes defined in the global tables. The disease conditions may also be identified using the NDC codes. The claims are assigned an age sequence by checking the age of the consumers in the claims against an age sequence table and assigning a sequence to the claims. Further, the claims are classified into categories and further classified into subcategories using the ICD9 codes. The most expensive subcategory for the consumer is reported and other subcategories are reported as comorbidities. The cost percentage of all disease conditions and the percentage of utilization or cost in a health plan are determined by the categorized claims. Furthermore, the CPT codes are classified into CPT groups called service categories. The step of processing the claims of the consumers includes generating a claim summary for the consumers based on the health plan of the consumers.

A plurality of costs of the health care organization are determined 104c using at least one or more of the health plan information of the consumers, the providers, the claims, and the hospitals. The plurality of costs includes utilization cost, liability costs, and paid costs. The utilization cost is the cost of health care service provided by the provider. The liability cost is the amount the health plan is liable to pay to the provider. The paid cost is the actual amount paid by the health plan to the provider. The step of determining the costs of the health care organization includes the calculation of a catastrophic value using the plurality of costs based on the claims of the consumer. The catastrophic value is calculated by dividing the sum of the plurality of costs by a predetermined scaling factor. The claims exceeding a predetermined limit on the total costs are assigned a particular catastrophic value. For example, the sum of the plurality of costs may be divided by a scaling factor of 1000. All claims exceeding a total cost of, for example, 99,999 dollars maybe assigned a catastrophic value of 99. A claim having a catastrophic value of, for example 21, indicates the total claim amount to be equal to or more than 21,000 dollars. Further the catastrophic value is used to identify consumers having maximum claim amount.

The claims originating from hospitals and health facilities are identified. The number of consumers admitted to the hospitals and the health facilities are determined. The referrals and the PCPs referring the consumers to the hospitals and the health facilities are identified. The cost of health care administered to the admitted consumers is calculated. Further, the length of stay of each admitted consumer is determined. The average length of stay of the consumers is calculated by dividing the sum of lengths of stay of all the admitted consumers by the total number of admitted consumers. Further, the claims are analyzed and classified under service categories. The services offered in each of the service categories are classified based on the revenues codes, CPT codes, ICD9P codes, DRG codes, and HCPCS codes. The Per Member Per Month (PMPM) cost of each of the services is calculated against the age range of the consumers, the PCPs, the employer groups, and the PCP networks.

The computer implemented method disclosed herein is used to assess 104d the performance of the providers for the health plan using the plurality of costs. The primary care physician is analyzed based on the entire population of the consumers associated with the primary care physician. In the population based analysis, the claims of all the consumers associated with the primary care physician are captured. The claims include costs incurred in the PCP's office and also include claims incurred in one of hospital, specialist's office, radiology lab, pharmacy, etc. The consumer's expenses vary depending on the age, gender, and the disease conditions of the consumer. A PCP may have more elderly consumers or may have sicker consumers. Hence, in the utilization analytics, the age, gender, and disease conditions of the consumers are adjusted. The age, gender, and disease conditions are adjusted by calculating the average cost in the health plan for each year of age and gender and then calculating the average cost of each disease by age and gender. Further, the number of consumers with a specific disease condition(s) for a PCP is analyzed. The expected cost due to the specific disease condition is determined for each consumer separately and for a combination of all the consumers associated with the PCP. Further, the actual cost is calculated for the consumers associated with a PCP. The total cost of all the consumers in a PCP's practice is determined and reported as the PCP's actual expense. The PCPs expense indicates the efficiency of the PCP in managing the patients' hospitalization and specialist service needs.

The step of assessing performance of the providers includes calculating a utilization performance ratio for ranking the providers. The utilization performance ratio is calculated for each PCP. The utilization performance ratio of the PCP is calculated as the ratio of the sum of the total actual cost of all the PCP's consumers to the sum of the total expected cost. The utilization performance ratio may be used for designing pay for performance programs for the PCPs. The method disclosed herein further includes calculating a composite index value for the PCP. The composite index value is determined by including a predetermined portion of the catastrophic value to the utilization performance ratio of the primary care physician.

PRG specialists perform medical procedures whereas the MRG specialists provide medical management of the consumers. The PRG specialists are analyzed based on service codes and the related costs for performing a medical procedure. The analysis comprises including all the claims falling within a predefined period of time around the date of the medical procedure. Further, the claims not connected to the medical procedure or the diagnosis, are excluded. The steps involved in analyzing the PRG specialists comprise the steps of identifying a performed medical procedure, identifying the time frames of cost calculation, searching for overlapping medical procedures, including all claims related to the medical procedure, excluding all claims not related to the medical procedure, adjusting and normalizing for the age and the gender of the consumer, and excluding the outlier specialists whose costs of medical procedure falls outside a predefined range. For example, if the cost of a medical procedure by a PRG specialist is greater than twice or less than half of the predefined cost, that PRG specialist is considered as an outlier and is excluded. Further, the average cost for a medical procedure, termed the expected cost for performing that procedure, is calculated. A performance index for the PRG specialist is calculated as the ratio of the actual costs of the all the medical procedures performed to the expected cost of all those medical procedures. Further, based on the cost of the medical procedure a performance index may be provided to the PCP referring the consumer to the selected PRG specialist.

The MRG specialists mostly provide medical management of the consumers and may not perform medical procedures. The MRG specialists are analyzed based on diagnosis codes. The steps involved in analyzing the cost incurred due to the medical services of MRG specialist are similar to that of the PRG specialist. Instead of analyzing the cost based on medical procedure, the costs of an MRG specialist are analyzed based on the medical services provided by the MRG specialist. The computer implemented method disclosed herein further comprises generating web reports of the performance analysis of the providers. The reports are used for designing pay for performance for the providers. The generated reports comprise admin actuarial reports, PCP analysis reports, PRG analysis reports, MRG analysis reports, catastrophic analysis reports, PCP network analysis reports, utilization analysis reports, employer group analysis reports, and hospital analysis reports.

The computer implemented method disclosed herein further comprises the step of generating reports of comparative relative value unit (RVU) utilization for a primary care physician. The RVU is used for evaluating the actual utilization and the comparative utilization by the PCP. The services provided by the PCP are associated with service codes such as the CPT codes. Further, the service code of a particular service provided by the PCP is associated with a RVU. The RVU of a particular service is based on the effort involved in delivering the particular service by the PCP to the consumers. By using service codes with RVU and applying proprietary methodology for service codes that do not have the RVU, the total RVU utilization for the PCP is calculated. Further, a comparative RVU utilization report comprising the PCP's actual RVU utilization as a ratio to the expected RVU utilization is generated. The expected RVU is adjusted for the age and the gender of the PCP's members.

Figure 2:
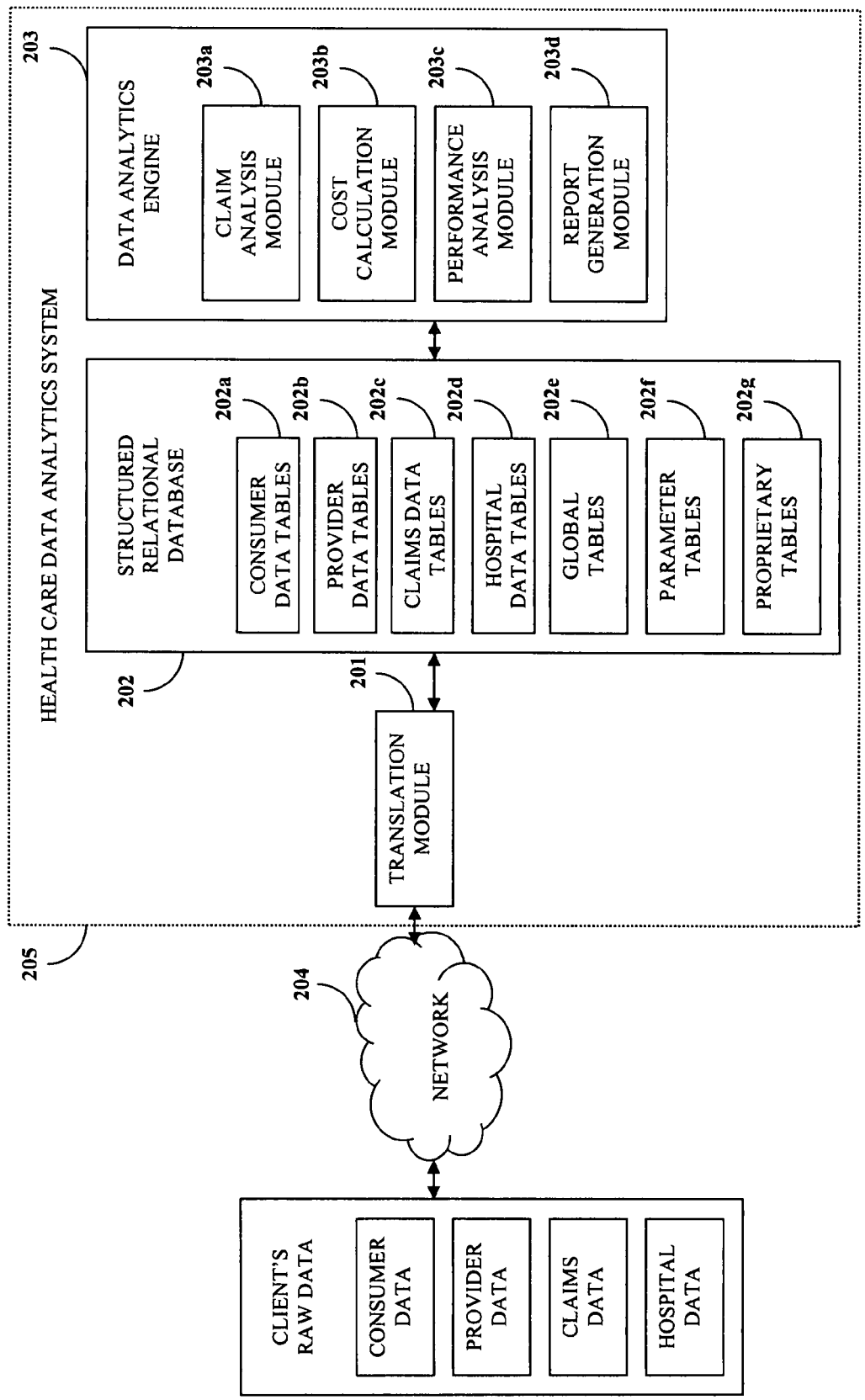
FIG. 2 illustrates a system for utilization analysis and performance evaluation of providers in a health care organization.

FIG. 2 illustrates a system for utilization analysis and performance evaluation of providers in a health care organization. The computer implemented system disclosed herein comprises a translation module 201, a structured relational database 202, and a data analytics engine 203. The translational module 201 translates and organizes the raw health care data in a structured relational format. The translation module 201 is used for creating file layouts, mapping fields of the health care data, and verifying for integrity and validity of the health care data. The translation module 201 receives consumer data of a health plan or a physician group providing health care services to the consumers, provider data, claims data, and hospital data in a raw format via a network 204. The translated health care data is stored in a structured relational format in a structured relational database 202. The structured relational database 202 comprises consumer data tables 202a, provider data tables 202b, claims data tables 202c, hospital data tables 202d, global tables 202e, parameter tables 202f, and proprietary tables 202g. The data analytics engine 203 comprises a claim analysis module 203a, a cost calculation module 203b, a performance analysis module 203c, and a report generation module 203d. The components of the health care data analytics system 205 communicate with each other.

The claim analysis module 203a processes the claims of the consumers enrolled in a health plan. The claims are processed to classify the claims based on age, gender, disease, and comorbid conditions of the consumer. The claim analysis module 203a further generates a claim summary of the processed claims. The step of processing the claims is described in the detailed description of FIG. 1. The cost calculation module 203b determines a plurality of costs of involved in providing health care services to the consumers in a health plan. The plurality of costs is determined using at least one or more of the health plan information of the consumers, the providers, the claims, and the hospitals. The plurality of costs comprises utilization costs, liability costs, and paid costs. The cost calculation module 203b assigns a catastrophic value to the claims based on the determined plurality of costs. The steps involved in the calculation and analysis of the plurality of costs are described herein under the detailed description of FIG. 1.

The performance analysis module 203c assesses the performance of a provider using the determined plurality of costs. The provider is one of a primary care physician, a procedurally related group specialist and a medically related group specialist. The performance of the providers is evaluated for the health plan using the plurality of costs. The performance analysis module 203c is used to analyze the PCPs based on the number of consumers associated with the PCPs. The total cost of all consumers in a PCP's practice is determined by the cost calculation module 203b and reported as the PCP's expense. The PCPs' comparative expense indicates the efficiency of the PCP in managing the patients' hospitalization and specialist service needs. The performance analysis module 203c evaluates the performance of PRG specialists and MRG specialists by analyzing the costs involved in performing medical procedures and managing medically by the specialist on the consumers. Further the performance analysis module 203c may assign a performance index to each of the providers using the comparative cost analysis data of the providers.

The performance analysis module 203c further calculates a utilization performance ratio of the PCP. Firstly, the total cost for a particular disease condition in the health plan is determined for each age and gender of the consumers. The total cost is divided by the number of consumers with that particular disease condition. Secondly, an average cost is determined for the particular disease condition for a particular age and gender of the consumers. The total average cost is determined based on the number of consumers in the PCP's practice of the particular age and gender and with the particular disease condition. The utilization performance ratio of the PCP is then calculated as the ratio of the sum of the total cost of all the members of the PCP to the sum of the average cost. The performance analysis module 203c calculates a composite index value for the PCP. The composite index value is determined by including a predetermined portion of the catastrophic value to the utilization performance ratio of the primary care physician. The performance analysis module 203c further calculates a total relative value unit (RVU) utilization for the PCP by using service codes with the RVU and applying proprietary methodology for service codes that do not have the RVU.

The report generation module 203d generates web reports of the utilization analysis and performance evaluation of the providers. The reports are used for designing pay for performance for the provider. The generated reports include administration actuarial reports, PCP analysis report, PRG analysis report, MRG analysis report, catastrophic analysis report, PCP network analysis report, utilization analysis report, employer group analysis report and hospital analysis report. The report generation module 203d further generates a comparative RVU utilization report comprising the PCP's actual RVU utilization as a ratio to the expected RVU utilization. The steps involved in the comparative RVU utilization reporting is described herein under the detailed description of FIG. 1.

It will be readily apparent that the various methods and algorithms described herein may be implemented in a computer readable medium appropriately programmed for general purpose computers and computing devices. Typically a processor, for e.g., one or more microprocessors will receive instructions from a memory or like device, and execute those instructions, thereby performing one or more processes defined by those instructions. Further, programs that implement such methods and algorithms may be stored and transmitted using a variety of media, for e.g., computer readable media in a number of manners. In one embodiment, hard-wired circuitry or custom hardware may be used in place of, or in combination with, software instructions for implementation of the processes of various embodiments. Thus, embodiments are not limited to any specific combination of hardware and software. A 'processor' means any one or more microprocessors, Central Processing Unit (CPU) devices, computing devices, microcontrollers, digital signal processors or like devices. The term 'computer-readable medium' refers to any medium that participates in providing data, for example instructions that may be read by a computer, a processor or a like device. Such a medium may take many forms, including but not limited to, non-volatile media, volatile media, and transmission media. Non-volatile media include, for example, optical or magnetic disks and other persistent memory volatile media include Dynamic Random Access Memory (DRAM), which typically constitutes the main memory. Transmission media include coaxial cables, copper wire and fiber optics, including the wires that comprise a system bus coupled to the processor. Transmission media may include or convey acoustic waves, light waves and electromagnetic emissions, such as those generated during Radio Frequency (RF) and Infrared (IR) data communications. Common forms of computer-readable media include, for example, a floppy disk, a flexible disk, hard disk, magnetic tape, any other magnetic medium, a Compact Disc-Read Only Memory (CD-ROM), Digital Versatile Disc (DVD), any other optical medium, punch cards, paper tape, any other physical medium with patterns of holes, a Random Access Memory (RAM), a Programmable Read Only Memory (PROM), an Erasable Programmable Read Only Memory (EPROM), an Electrically Erasable Programmable Read Only Memory (EEPROM), a flash memory, any other memory chip or cartridge, a carrier wave as described hereinafter, or any other medium from which a computer can read. In general, the computer-readable programs may be implemented in any programming language. Some examples of languages that can be used include C, C++, C#, or JAVA. The software programs may be stored on or in one or more mediums as an object code. A computer program product comprising computer executable instructions embodied in a computer-readable medium comprises computer parsable codes for the implementation of the processes of various embodiments.

Where databases are described such as the structured relational database 202, it will be understood by one of ordinary skill in the art that (i) alternative database structures to those described may be readily employed, and (ii) other memory structures besides databases may be readily employed. Any illustrations or descriptions of any sample databases presented herein are illustrative arrangements for stored representations of information. Any number of other arrangements may be employed besides those suggested by, e.g., tables illustrated in drawings or elsewhere. Similarly, any illustrated entries of the databases represent exemplary information only; one of ordinary skill in the art will understand that the number and content of the entries can be different from those described herein. Further, despite any depiction of the databases as tables, other formats including relational databases, object-based models and/or distributed databases could be used to store and manipulate the data types described herein. Likewise, object methods or behaviors of a database can be used to implement various processes, such as the described herein. In addition, the databases may, in a known manner, be stored locally or remotely from a device that accesses data in such a database.

The present invention can be configured to work in a network environment including a computer that is in communication, via a communications network, with one or more devices. The computer may communicate with the devices directly or indirectly, via a wired or wireless medium such as the Internet, Local Area Network (LAN), Wide Area Network (WAN) or Ethernet, Token Ring, or via any appropriate communications means or combination of communications means. Each of the devices may comprise computers, such as those based on the Intel® processors, AMD® processors, UltraSPARC® processors, etc. that are adapted to communicate with the computer. Any number and type of machines may be in communication with the computer.

The foregoing examples have been provided merely for the purpose of explanation and are in no way to be construed as limiting of the present method and system disclosed herein. While the invention has been described with reference to various embodiments, it is understood that the words, which have been used herein, are words of description and illustration, rather than words of limitation. Further, although the invention has been described herein with reference to particular means, materials and embodiments, the invention is not intended to be limited to the particulars disclosed herein; rather, the invention extends to all functionally equivalent structures, methods and uses, such as are within the scope of the appended claims. Those skilled in the art, having the benefit of the teachings of this specification, may effect numerous modifications thereto and changes may be made without departing from the scope and spirit of the invention in its aspects.

We claim:

1. A computer implemented method of utilization analysis and performance evaluation of providers in a health care organization, comprising the steps of:
   collecting health care data over a network, wherein said health care data comprises health plan information of consumers, said providers, claims, and hospitals;
   analyzing said collected health care data for said utilization analysis and said performance evaluation of the providers using a data analytics engine stored on said computer, comprising the steps of:
      determining a plurality of costs of said health care organization using at least one or more of the health plan information of the consumers, the providers, the claims, and said hospitals;
      calculating an average cost of the health plan adjusted for a specific age, sex and disease condition of the consumers;
      determining an expected cost for each consumer in the health plan based on said average cost and a number of consumers of the specific age, sex and disease condition;
      storing said expected cost for the consumer in a database;
      determining a total expected cost for the disease condition by summing expected costs for all the consumers of the specific age, sex and disease condition in the health plan;
      calculating a total actual cost for all the consumers associated with each of the providers using said health plan information; and
      assessing performance of the providers for said health plan, comprising calculating a utilization performance ratio of a provider to rank said provider, wherein said data analytics engine calculates said utilization performance ratio as a ratio of a sum of the total actual cost of the consumers associated with the provider to a sum of total expected cost for the consumers, adjusted for the age, the sex and the disease condition;
   whereby the utilization and performance of the providers in providing health care to the consumers are evaluated by analyzing the health care data.

2. The computer implemented method of claim 1, further comprising the step of calculating consumer statistics of the consumers comprising calculating the period of enrollment of the consumers for the health plan.

3. The computer implemented method of claim 2, wherein said step of calculating consumer statistics of the consumers for the health plan is performed periodically.

4. The computer implemented method of claim 1, further comprising the step of processing the claims of the consumers to classify the claims based on age, gender, disease, and comorbid conditions of the consumers, wherein the step of processing claims of the consumers comprises generating a claim summary for the consumers based on the health plan of the consumers.

5. The computer implemented method of claim 4, wherein said classified claims are used to identify disease conditions having maximum claim amount, wherein the plurality of costs includes said claim amount.

6. The computer implemented method of claim 1, further comprising calculating a catastrophic value using the plurality of costs based on the claims of the consumers.

7. The computer implemented method of claim 6, wherein said catastrophic value is used to identify consumers having maximum claim amount wherein the plurality of costs includes said claim amount.

8. The computer implemented method of claim 1, further comprising generating web reports of said performance analysis of the providers, wherein said reports are used for designing pay for performance for the providers.

9. The computer implemented method of claim 8, wherein said reports comprise administration actuarial reports, primary care physician analysis reports, procedurally related group specialist analysis reports, medically related group specialist analysis reports, catastrophic cost analysis reports, primary care physician network analysis reports, utilization analysis reports, employer group analysis reports, hospital expenses analysis reports and reports of comparative relative value unit (RVU) utilization for each of said primary care physicians.

10. The computer implemented method of claim 1, further comprising calculating a performance index of each specialist provider by evaluating performance of said specialist provider, wherein said data analytics engine evaluates said performance of said specialist provider by analyzing costs involved in performing one of medical procedures and medical management of said consumers by said specialist provider, wherein said specialist provider is a procedurally related group (PRG) specialist, and wherein said step of evaluating performance of said PRG specialist comprises:
   identifying a medical procedure performed by said PRG specialist;
   identifying time frames of cost calculation for said performed medical procedure;
   including all claims related to said medical procedure and excluding claims not related to said medical procedure; and
   adjusting and normalizing for the age and the sex of the consumer.

11. The computer implemented method of claim 10, wherein said step of analyzing costs involved in performing medical procedures comprises calculating a ratio of the actual costs of said medical procedures performed by said PRG specialist provider to the expected cost of said medical procedures.

12. The computer implemented method of claim 1, wherein the consumers are one of an individual member, a medicare member, a medicaid member, and an employer, wherein said employer provides health care benefits to a plurality of employees through the health plan.

13. The computer implemented method of claim 1, wherein the providers are one of a primary care physician and a specialist provider, wherein said specialist provider is one of a procedurally related group specialist, and a medically related group specialist.

14. The computer implemented method of claim 1, further comprising the step of analyzing a primary care physician based on entire population of the consumers associated with said primary care physician.

15. The computer implemented method of claim 1, further comprising the step of organizing said health care data comprising storing the health care data in a plurality of standard tables in a structured relational format.

16. The computer implemented method of claim 1, wherein the plurality of costs comprises utilization cost, liability cost, and paid cost of the consumers for the health plan.

17. The computer implemented method of claim 1, wherein said step of assessing performance of the providers comprises calculating relative value unit utilization for primary care physicians, wherein said relative value unit utilizations of said primary care physicians are used to generate a comparative relative value unit utilization report of the primary care physicians.

18. The computer implemented method of claim 1, further comprising calculating a composite index value for a primary care physician by including a predetermined portion of the catastrophic value to a utilization performance ratio of the primary care physician.

19. The computer implemented method of claim 1, wherein the total actual cost of all the consumers associated with each primary care physician comprises cost incurred at said primary care physician, hospitalizations costs and non-hospital expenses.

20. The computer implemented method of claim 1, wherein said data analytics engine determines said expected cost due to specific disease condition for each consumer separately and for a combination of all the consumers associated with each primary care physician.

21. A computer implemented healthcare data analytics system comprising one or more processors for utilization analysis and performance evaluation of providers in a health care organization, said healthcare data analytics system comprising:
  a structured relational database for storing health care data in said structured relational format, wherein said health care data comprises health plan information of consumers, said providers, claims, and hospitals;
  a data analytics engine stored on said one or more processors for said utilization analysis and said performance evaluation of the providers, comprising:
    a cost calculation module for determining a plurality of costs of a health care organization using at least one or more of the health plan information of said consumers, the providers, said claims, and said hospitals, wherein said cost calculation module performs one or more of the steps of:
      calculating an average cost of the health plan adjusted for a specific age, sex and disease condition of the consumers;
      determining an expected cost for each consumer in the health plan based on said average cost and a number of consumers of the specific age, sex and disease condition;
      storing said expected cost for the consumer in a database;
      determining a total expected cost for the disease condition by summing expected costs for all the consumers of the specific age, sex and disease condition in the health plan;
      calculating a total actual cost for all the consumers associated with each of the providers using said health plan information; and
    a performance analysis module for assessing performance of the providers, wherein said performance analysis module calculates a utilization performance ratio of a provider to rank said provider, wherein said performance analysis module calculates said utilization performance ratio as a ratio of a sum of the total actual cost of the consumers associated with the provider to a sum of total expected cost for the consumers, adjusted for the age, the sex and the disease condition.

22. The computer implemented system of claim 21, further comprising a claim analysis module for generating a claim summary for the consumers based on a health plan.

23. The computer implemented system of claim 21, further comprising a report generation module for generating web reports of performance analysis of the providers, wherein said reports are used for designing pay for performance for the providers.

24. A computer program product comprising computer executable instructions embodied in a non-transitory computer-readable medium, wherein said computer program product comprises:
  a first computer parsable program code for collecting health care data, wherein the health care data comprises health plan information of consumers, the providers, claims, and hospitals;
  a second computer parsable program code for analyzing the collected health care data for the utilization analysis and the performance evaluation of the providers;
  a third computer parsable program code for determining a plurality of costs of the health care organization using at least one or more of the health plan information of the consumers, the providers, the claims, and the hospitals, comprising the steps of:
    calculating an average cost of the health plan adjusted for a specific age, sex and disease condition of the consumers;
    determining an expected cost for each consumer in the health plan based on said average cost and a number of consumers of the specific age, sex and disease condition;
    storing said expected cost for the consumer in a database;
    determining a total expected cost for the disease condition by summing expected costs for all the consumers of the specific age, sex and disease condition in the health plan;
    calculating a total actual cost for all the consumers associated with each of the providers using said health plan information; and
  an fourth computer parsable program code for assessing performance of the providers for the health plan using the plurality of costs, comprising calculating a utilization performance ratio of a provider to rank said provider, wherein said data analytics engine calculates said utilization performance ratio as a ratio of a sum of the total actual cost of the consumers associated with the provider to a sum of total expected cost for the consumers, adjusted for the age, the sex and the disease condition.

* * * * *